United States Patent
Roger et al.

(10) Patent No.: US 10,420,592 B2
(45) Date of Patent: Sep. 24, 2019

(54) ROD REDUCTION DEVICE

(71) Applicant: Spinal Developments Pty Ltd, A.T.F. The Spinesr Unit Trust, North Sydney, New South Wales (AU)

(72) Inventors: Gregory Roger, St Leonards (AU); Davor Saravanja, Roseville (AU)

(73) Assignee: SPINAL DEVELOPMENTS PTY LTD, A.T.F. THE SPINESR UNIT TRUST, North Sydney, New South Wales (AU)

( * ) Notice: Subject to any disclaimer, the term of this patent is extended or adjusted under 35 U.S.C. 154(b) by 19 days.

(21) Appl. No.: 15/525,530

(22) PCT Filed: Nov. 9, 2015

(86) PCT No.: PCT/AU2015/050695
§ 371 (c)(1),
(2) Date: May 9, 2017

(87) PCT Pub. No.: WO2016/074030
PCT Pub. Date: May 19, 2016

(65) Prior Publication Data
US 2017/0325855 A1    Nov. 16, 2017

(30) Foreign Application Priority Data
Nov. 10, 2014   (AU) ................................ 2014904503

(51) Int. Cl.
*A61B 17/88*    (2006.01)
*A61B 17/70*    (2006.01)

(52) U.S. Cl.
CPC ...... *A61B 17/7085* (2013.01); *A61B 17/7086* (2013.01)

(58) Field of Classification Search
CPC .................. A61B 17/7085; A61B 17/7086
USPC ................... 606/264, 279, 99, 86 A
See application file for complete search history.

(56) References Cited

U.S. PATENT DOCUMENTS

| | | | |
|---|---|---|---|
| 5,720,751 A * | 2/1998 | Jackson | A61B 17/7032 606/104 |
| 7,572,264 B2 * | 8/2009 | Null | A61B 17/862 606/104 |
| 2005/0149036 A1 | 7/2005 | Varieur et al. | |
| 2007/0073294 A1 * | 3/2007 | Chin | A61B 17/7037 606/86 A |
| 2007/0282337 A1 | 12/2007 | Garamszegi | |
| 2008/0015601 A1 | 1/2008 | Castro et al. | |
| 2008/0172062 A1 * | 7/2008 | Donahue | A61B 17/7037 606/104 |
| 2009/0143828 A1 * | 6/2009 | Stad | A61B 17/7085 606/86 A |
| 2010/0324609 A1 | 12/2010 | Jones et al. | |

* cited by examiner

*Primary Examiner* — Pedro Philogene
*Assistant Examiner* — David C Comstock
(74) *Attorney, Agent, or Firm* — Browdy and Neimark, P.L.L.C.

(57) ABSTRACT

An orthopedic bone rod reduction device and method is disclosed. The device includes an actuator having a drive surface and a bone rod engagement element for engaging with a bone rod. The assembly further includes a spring positioned between the drive surface of the actuator and the rod engagement element. The rod reduction assembly controls movement of a bone rod relative to a bone anchor positioned in a bone.

20 Claims, 3 Drawing Sheets

ROD REDUCTION DEVICE

The present application claims priority from Australia provisional patent application number 2014904503 filed 10 Nov. 2014, the contents of which are herein incorporated.

TECHNICAL FIELD

The present disclosure relates to devices and methods for stabilising parts of the body. In particular, the devices and methods are for use in the reduction of stabilising rods in orthopedic surgery.

BACKGROUND

During spinal fusion surgery and surgery to correct scoliosis, the curves of the spine are realigned. Particularly in scoliosis correction surgery this may involve relatively large translations of individual vertebrae to achieve the desired spinal alignment, the realigned vertebrae fixed in place by a combination of shaped rods and pedicle screws.

Prolonged degenerative disease processes and the distortions that occur as a result of severe scoliosis are such that the forces required to move the spinal column to the new curves are considerable. In addition, the translations required of each pedicle screw in order to match up to the shaped rod are often relatively large. These two factors render the matching of the screws with a rod to which they are to be connected during surgery difficult.

Various "rod approximating" devices have been designed in attempt to assist with this procedure. Such devices are connected to a screw to force a rod into the screw head. Many of these devices may be used during a single surgery with up to 20, 10 each side, connected to the screws in a scoliosis surgery.

However, the current rod approximating devices do not spread the force generated in re-shaping the spine evenly over all the screws. Due to their stiff construct they more typically load up two or at most three screws with the consequent force. This in turn risks pulling the screws out of the bone or weakening the screws' grip in the bone, which may in turn cause failure of the surgery or increased surgical complication intraoperatively.

There is a need, therefore, to address the problems associated with current devices used in rod reduction.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

An orthopedic rod reduction device comprising:
an actuator having a drive surface;
a rod engagement element for engaging a rod and moving the rod upon movement of the actuator, and
a spring positioned between the drive surface of the actuator and the rod engagement element.

A method of supporting the spinal column of a patient including:
providing a plurality of rod reduction devices, wherein each rod reduction device comprises:
an actuator having a drive surface;
a rod engagement element for engaging a rod and moving the rod upon movement of the actuator, and
a spring member positioned between the drive surface of the actuator and the rod engagement element;
actuating the actuator to cause the rod engagement element to advance the rod towards a bone anchor; and
maintaining a controlled force between the rod engagement element and the rod upon movement of the rod relative to the actuator.

The device may further include a bone anchor engagement element to secure the device to a respective bone anchor.

The drive surface of the device may be any surface which imparts a direct force on the spring. The drive surface may be located on the actuator or on a second drive head. The drive surface may be an internal or an external surface of the device.

The spring may be housed within at least part of the actuator. In another embodiment, the spring may be positioned external to the actuator.

The spring of the device may impart a force on the rod engagement element to thereby maintain a force on a target portion of an elongate rod even if forces applied to other portions of the rod cause movement of the target portion of the rod relative to the actuator.

The spring of the device may be a resiliently flexible member made from a suitable material. The material may be metallic or non-metallic.

The device may include a plurality of springs. In this embodiment, the springs may be positioned in parallel relative to each other. Alternatively, the springs may be in series relative to each other.

In one embodiment, the spring is a helically wound coil. The coil may be made from any suitable metal, metal alloy or plastic material.

In a further embodiment, the spring may be made from a metal or plastic which is cut to provide resilient flexibility. The spring may be made from a sheet of a metal alloy such as titanium or Nitinol.

In another embodiment, the spring comprises a hydraulic spring. In a still further embodiment, the spring comprises a pneumatic spring.

The rod reduction device of the present disclosure may be used for a number of surgical indications and in particular for orthopedic procedures. In one embodiment, the device is used to fix a target portion of rod to a bone anchor in a procedure to correct a deformity of the spinal column. In such a procedure, a plurality of bone anchors are implanted into adjacent vertebrae of a patient and a pre-shaped rod aligned with and fixed to the bone anchors along a length of the spine. The bone anchors may have a head with a recessed seat to receive the rod and a screw threaded shaft for insertion into the bone.

The rod reduction device may further comprise a support. The support may have a passage at least partially therethrough to receive at least part of the actuator. In one embodiment, the support comprises a proximal head having an upper surface and a lower surface and a passage therethrough. The passage may extend from a substantially central region of the upper surface through to an opening in a substantially central region of the lower surface.

The passage of the proximal head of the support may be defined by at least one internal wall of the proximal head. The at least one internal wall may be continuous and define a substantially circular cross sectional passage. Preferably, at least a portion of the internal wall(s) of the proximal head includes a thread disposed thereon. In one embodiment, the thread may comprise a buttress thread. Alternatively, the thread may be a round thread or a square thread.

The actuator may comprise a drive head and a drive shaft. The drive shaft may extend from the drive head and may include a threaded outer surface. Typically, the threaded outer surface of the drive shaft is configured to threadingly engage with the thread of the internal wall(s) of the proximal head of the support.

The drive head may be any shape and is typically configured for ease of handling by a user. In one embodiment, the drive head may comprise an upper face and an opposed lower face and at least one sidewall extending therebetween. The drive head may include a number of sidewalls or may comprise a continuous smooth side wall. In one embodiment, the drive head comprises 2, 3, 4, 5, 6, 8, 9 or 10 sidewalls. In a particular embodiment, the drive head may comprise a hex nut configuration to enable a user to readily rotate the drive head either manually or with a suitable instrument.

In an embodiment wherein the drive head comprises a continuous sidewall, the sidewall may comprise a plurality of ridges or a roughened surface to enhance the grip of a user.

The drive head is rotatably moveable relative to the support by either manually applying rotational force or using a suitable instrument. By virtue of its connection to the drive head, rotation of the drive head similarly rotates the drive shaft relative to the support.

When the drive shaft and the proximal head of the support are in threaded engagement, rotation of the drive head effects a linear translational movement of the drive head and drive shaft relative to the proximal head.

In one embodiment, the drive shaft engages the rod engagement element such that any linear movement of the actuator imparts a linear translational movement of the rod engaging element, without rotating the rod engaging element.

The drive shaft typically extends from a proximal end connected to the drive head to a distal end which is mounted to the rod engagement element. The drive shaft may include an elongate internal cavity which may at least partially house the spring of the device.

The spring may extend from a proximal end to a distal end at least partially within the housing of the drive shaft. The proximal end of the spring may be in engagement with the lower face of the drive head. In this embodiment, the drive surface comprises at least part of the lower face of the drive head.

The distal end of the drive shaft may be connected to part of the rod engagement element. Further, the distal end of the spring may engage a portion of the rod engagement member.

The drive shaft may be a substantially straight tubular structure and may include a threaded outer surface. In one embodiment the rod engagement element includes a spring engagement element which extends from the rod engagement element and may be received within the tubular housing of the drive shaft. The spring engagement element may engage the distal end of the spring. Typically, the spring engagement element is a relatively rigid structure.

When the drive shaft and the proximal head of the support are in threaded engagement, rotation of the drive head effects the linear translational movement of the drive head and drive shaft relative to the proximal head. The relatively rigid spring engagement element may impart a force against the internally housed spring as the drive head and shaft are rotated and linearly translated relative to the proximal head of the support.

Typically, compression of the spring between the actuator and the rod engagement element causes the spring to move from a first natural state to a second energy absorbing state. The mechanism of movement between one state and another depends upon the nature of the spring. In one embodiment, where the spring is an elongate helical coil, the coil is caused to move from a natural state having a defined length along a longitudinal axis to an energy absorbing state wherein the coil is compressed and the length of the spring in the second state is less than the length in the first state.

The configuration of the spring may be such that its second state is achieved by a pre-determined number of rotations of the drive head which causes a certain length of linear movement of the drive head and the drive shaft relative to the support. Thus, the spring may be essentially loaded by the initial rotations of the drive head and thereafter once the spring is in its second state, the majority of the rotational movement of the drive head and drive shaft effects linear movement of the rod engagement member (only as much as the spring does not absorb this translation). It should be appreciated that during the initial rotations of the drive head there may be some linear translation of the rod engagement element.

In another aspect, there is provided an orthopedic rod reduction device comprising:
  an actuator having a first drive head and a second drive head, a drive shaft extending between said first and second drive heads;
  a rod engagement element for engaging a rod and moving the rod upon movement of the actuator, and
  a spring positioned between the second drive head of the actuator and the rod engagement element.

In this aspect, rather than internally housed within the drive shaft, the spring is positioned external to the drive shaft. The second drive head may comprise a lower spring engaging surface. The drive surface may be a portion of the lower spring engaging surface.

The spring may be positioned between and connected to the lower spring engaging surface and the rod engagement element. Typically, force of the second drive head on the spring causes the spring to move from a first natural state to a second energy absorbing state. Again, the mechanism of movement between one state and another depends upon the nature of the spring. In one embodiment, where the spring is an elongate helical coil, the coil is caused to move from a natural state having a defined length along a longitudinal axis to an energy absorbing state wherein the coil is compressed and the length of the spring in the second state is less than the length in the first state. Because the spring in this embodiment is connected to the lower spring engaging surface of the second drive head and the rod engagement element, transition from the first state of the spring to its second state brings the second drive head and the rod engagement element relatively closer together.

As above, the configuration of the spring of this embodiment may be such that its second state is reached upon a pre-determined number of rotations of the first drive head. Thus, the spring may be essentially loaded by the initial rotations of the first drive head and thereafter once the spring is in its second state, the majority of the rotational movement of the first drive head and drive shaft effects linear movement of the rod engagement member.

In another aspect, there is provided an orthopedic bone rod reduction assembly comprising:
  a support comprising a proximal head having a threaded passage therethrough and a bone anchor engaging portion extending from the proximal head;

an actuator comprising a drive head and an elongate drive shaft extending therefrom;

a bone rod engagement element for engaging with and moving the bone rod, the bone rod engagement element comprising a base member and a spring engagement element, a spring extending from a first end which engages the drive head to a second end which engages the spring engagement element of the rod engagement element, wherein the spring is moveable from a natural state to a compressed state by rotation of the drive head relative to the support;

wherein the spring is moved to its compressed state by a pre-determined number of rotations of the drive head after which, further rotation of the drive head causes a linear movement of the bone rod engagement element.

In a still further aspect, there is provided an orthopedic bone rod reduction assembly comprising:

a support comprising a proximal head having a threaded passage therethrough and a bone anchor engaging portion extending from the proximal head;

an actuator comprising a first drive head, a second drive head and an elongate drive shaft extending therebetween;

a bone rod engagement element for engaging with and moving the bone rod, the bone rod engagement element comprising a base member and a spring engagement element, a spring extending from a first end which engages the second drive head to a second end which engages the spring engagement element of the rod engagement element, wherein the spring is moveable from a natural state to a compressed state by rotation of the first drive head relative to the support;

wherein the spring is moved to its compressed state by a pre-determined number of rotations of the first drive head after which, further rotation of the first drive head causes a linear movement of the bone rod engagement element.

A plurality of the disclosed devices may be used to reduce a rod to a plurality of bone anchors. In this embodiment, it is envisaged that the plurality of devices may be connected to a central driver to act on the drive heads of the plurality of devices.

The devices of the present disclosure may be used in fusion surgery or surgery to correct scoliosis.

The disclosed devices may ameliorate uneven spreading of the load onto the anchor members. The above described spring system ensures that the load on a bone anchor is maintained through a range of translations of the rod so that as each rod reduction device forces the rod towards the bone anchor to which it is attached and thereby moves the rod with reference to the other bone anchors. The rod reduction devices on the other bone anchors maintain a displacing force on the rod, urging it towards its bone anchor, throughout a range of movement of the rod towards the bone anchors.

In an embodiment where, for example, 10 bone anchors and associated bone are urged towards a rod, each bone anchor is associated with a rod reduction device. With the rod held between the bone anchor and the rod reduction device, the rod reduction devices may then be advanced so as to partly move the rod towards the bone anchor and "load up" the spring so that as each device is advanced, sequentially or in unison, the load is divided more or less equally across the 10 bone anchors. This may continue until all of the bone anchors receive the rod and the new spinal shape is achieved.

The term "proximal" as used herein refers to the end of the device that is closer to the user and the term "distal" refers to the end of the device that is further from the user.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF THE DRAWING

FIG. 4a is a side view of a device of the present disclosure;

FIG. 4b is a cross sectional view of the device of FIG. 4a;

FIG. 5b is a cross sectional view of the device of FIG. 5a.

DESCRIPTION OF EXEMPLARY EMBODIMENTS OF THE DISCLOSURE

Figures 4A, 4B:
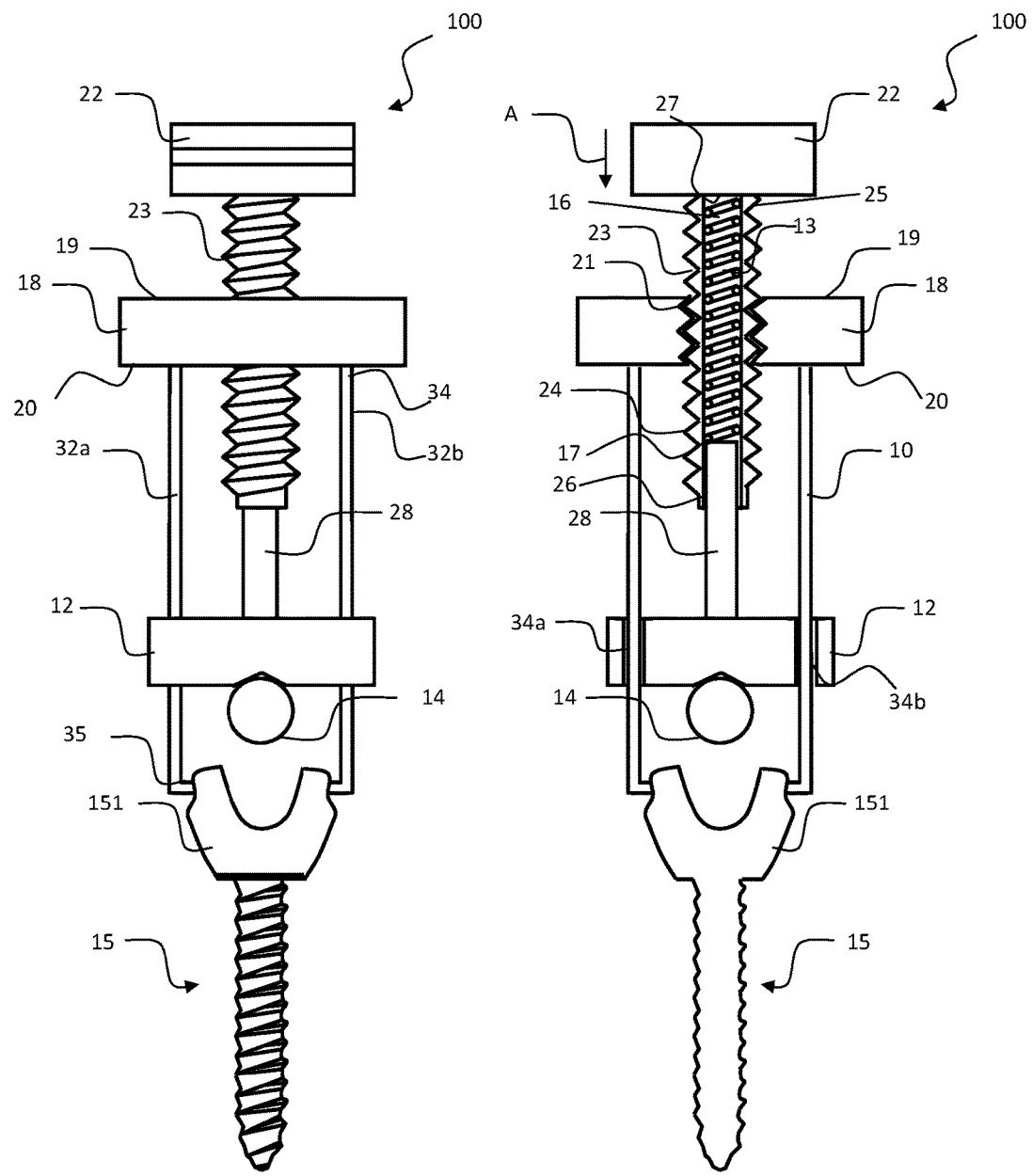
Figure 5A:
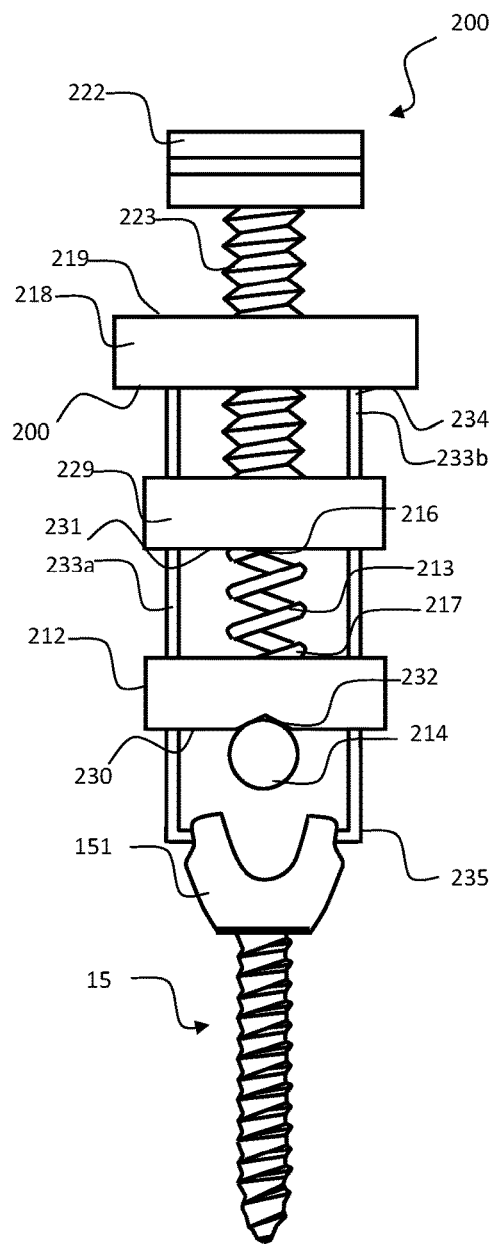
FIG. 5a is a side view of a device of another embodiment of the present disclosure.
Figure 5B:
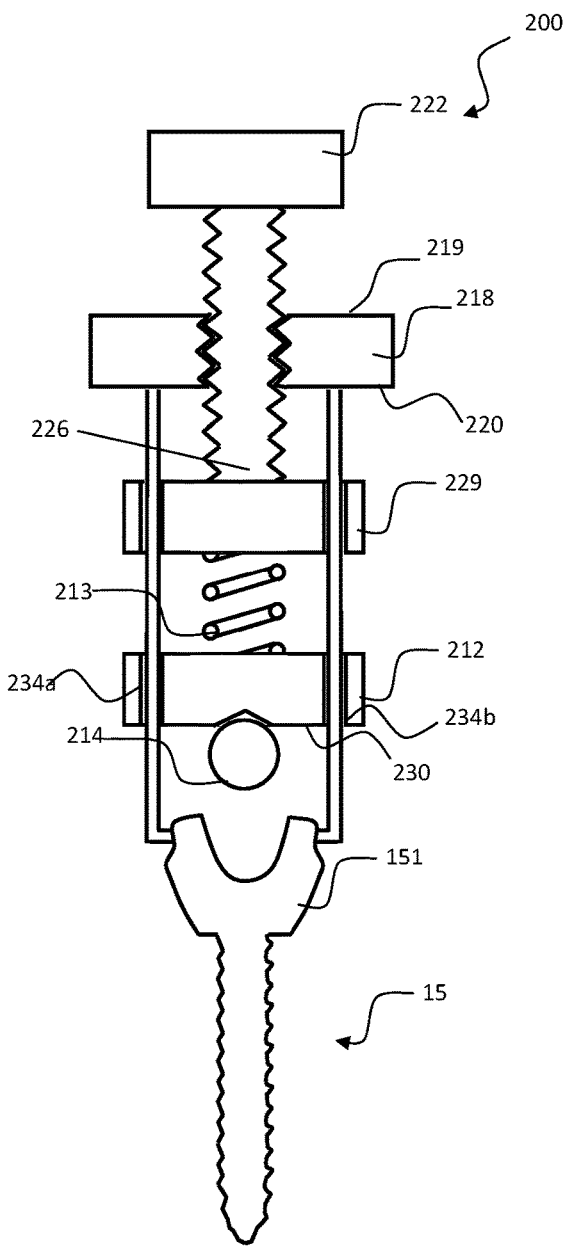

An actuator 11, rod engagement element 12 and a spring 13 are shown in FIGS. 1a to 1c, 2a and 2b. These elements may be included as part of a rod reduction device 100 as shown in FIGS. 4a and 4b, or a rod reduction device 200 as shown in FIGS. 5a and 5b.

Devices 100, 200 are used to reduce a rod 14 into a bone anchor 15. Spring 13 is configured to impart a force on rod engagement element 12 such that rod engagement element 12 maintains a controlled force on rod 14 even if external forces cause movement of rod 14 relative to actuator 11.

Figures 1A, 1B, 1C:
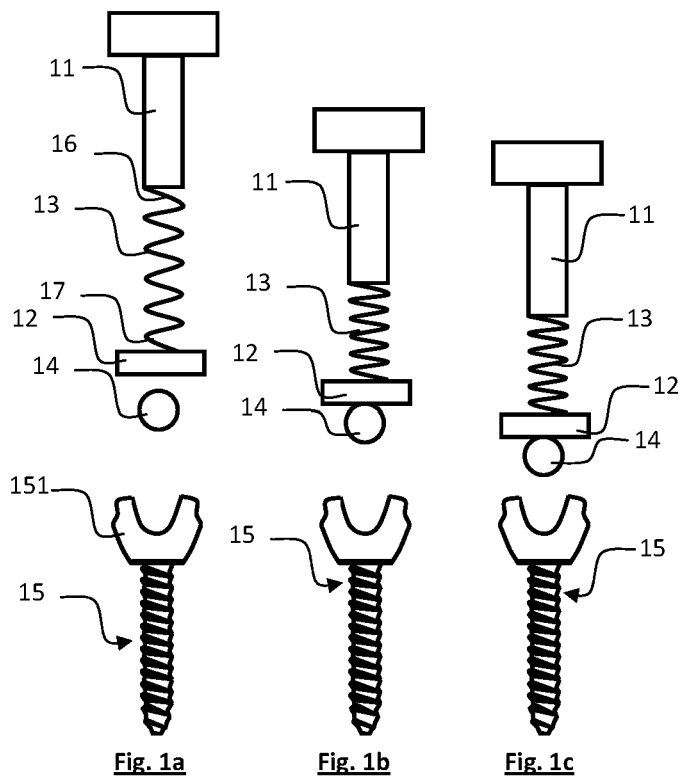
FIGS. 1a, 1b and 1c depict schematically, certain elements used in a device of the present disclosure.

In FIG. 1, spring 13 is in a natural state connected at a proximal end 16 to actuator 11 and at a distal end 17 to rod engagement element 12. Rod 14 is positioned above anchor 15 ready for reduction into a head 151 of anchor 15. In FIG. 1b, the actuator 11 is shown to have moved linearly towards bone anchor 15. While details of the linear movement of the actuator will be described in more detail below in relation to rod reduction devices 100, 200, movement from the position of actuator 11 in FIG. 1a, to the position of actuator 11 in FIG. 1b causes compression of spring 13. While a helical spring is depicted in these figures for simplicity, it is envisaged that other types of springs previously mentioned may be used. The spring, whatever type, is caused to move from a natural state depicted for example in FIG. 1a to a second, energy storing state, depicted for example in FIG. 1b, by virtue of the rod engagement element moving into contact with, and applying a force to, the rod 14.

Further linear movement of the actuator 11 towards bone anchor 15 as shown in FIG. 1c substantially linearly translates the rod engagement element and thus the engaged rod 14 towards head 151 of bone anchor 15. While there may be a slight further compression or expansion of spring 13 during this step, the majority of the movement comprises linear movement of the actuator 11 and the rod engagement element 12.

Figures 2A, 2B, 3A, 3B:
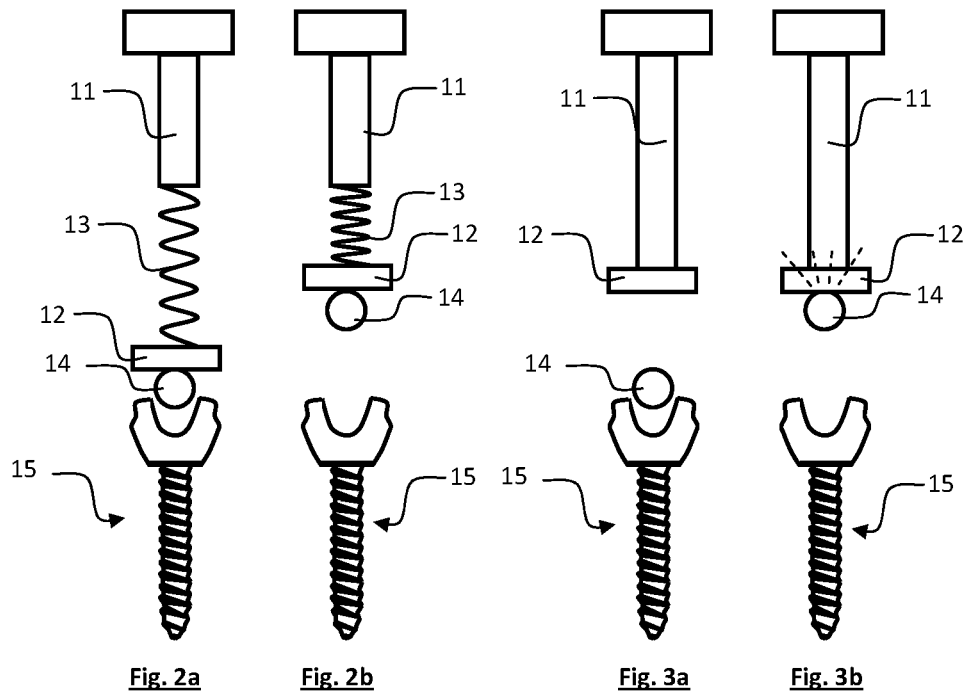
FIGS. 2a and 2b depict the components of FIGS. 1a, 1b and 1c, in use.
FIGS. 3a and 3b shows schematically a known system without a spring when in use.

An important feature of this arrangement is that the rod engagement element 12 is kept in a force applying engagement with rod 14. Therefore, if external forces during a procedure cause the rod to move towards anchor 15, the spring releases its energy and moves back towards its natural state to maintain a force on the rod engagement element 12 and therefore the rod 14. An example of this can be seen in FIG. 2a, wherein the depicted portion of rod 14 has been caused to drop towards the anchor 15 due to manipulation of other parts of the rod. The spring 13 moves towards its natural state configuration to cause the rod engagement element to "chase" rod 14 and maintain some force upon it. A comparative example in relation to this scenario, where a rod reduction device is provided without a spring between the actuator and the rod engagement element is represented in FIG. 3a. In this example, again the rod has been manipulated such that it drops towards anchor 15 but the rod engagement element is static and loses contact with rod 14.

In a scenario where manipulation of the rod downstream or upstream of the portion of rod 14 depicted in FIG. 2b causes that portion of rod 14 to be urged away from the bone anchor 15, spring 13 compresses, absorbing some of the force exerted by the rod 14 on the rod engagement element 12. A comparative example in relation to this scenario, where a rod reduction device is provided without a spring between the actuator 11 and the rod engagement element 12 is represented in FIG. 3b. In this example, again the rod has been manipulated such that it is urged away from the bone anchor 15, but the rod engagement element is static and bears the full force imparted by rod 14.

The elements described above in relation to FIGS. 1a to 2b are present in a rod reduction device 100 according to an embodiment of the present disclosure, as illustrated in FIGS. 4a and 4b, which is used to position rod 14 in a bone anchor 15 as part of a procedure to correct a deformity of the spinal column. While a single device 100 and only part of rod 14 (segments) are depicted in the Figures, the device 100 would usually be used as part of a larger system comprising a plurality of rod reduction devices 100, respectively positioned over bone anchors in the vertebrae of a patient and an elongate rod to be fixed to the bone anchors along a length of the spine.

Rod 14 is usually pre-shaped as desired and positioned over the bone anchors 15. Devices 100 force segments of rod 14 into respective anchor heads 15. In this regard, a surgeon typically progressively reduces various rod segments along the rod length until the entire rod is fixed to respective anchors and the vertebrae forced into the shape of the rod 14. However, given the range of forces and shifting of forces along the rod during the rod reduction, many segments of rod 14 undergo excessive changes of load. For example, as a segment of rod is manipulated using one rod reduction device 100, the forces between a different segment of rod and another of the rod reduction devices 100 can change significantly. Depending on the direction of the forces, in some instances they may be sufficient to cause the anchors to be pulled from the bone, or cause the rod to disengage from a rod reduction device.

The device 100 provides a means to maintain a relatively constant force against the rod segments, including absorbing any excessive forces during a surgical procedure.

As shown in FIGS. 4a and 4b, rod reduction device 100 comprises actuator 11, rod engagement element 12 and spring 13.

Rod reduction device 100 further comprises a support having a main body 18 which has an upper surface 19, lower surface 20 and a passage 21 therethrough.

Passage 21 receives actuator 11 in a threaded engagement as shown in FIG. 4b.

Actuator 11 comprises a drive head 22 and a drive shaft 23 which depends from drive head 22 and has an outer threaded surface 24.

Rotation of drive head 22 effects a linear translational movement of the drive head 22 and drive shaft 23 relative to main body 18 as depicted by Arrow A.

In FIG. 4b, spring 13 is internally housed within part of drive shaft 23. Drive shaft 23 extends from a first end 25 connected to the drive head 22 to second end 26. Spring 13, housed within drive shaft 23, extends from proximal end 16 to distal end 17. Proximal end 16 of spring 13 is in engagement with a lower surface 27 of drive head 22.

As shown in FIGS. 4a and 4b, drive shaft 23 comprises a tubular structure with an outer threaded surface 23. While fixed at first end 25 to drive head 22, a second end 26 of drive shaft 23 is open and slidably receives a rigid spring engagement shaft 28 which is connected to, or forms part of, rod engagement element 12.

With drive shaft 23 and main body 18 in threaded engagement, rotation of drive head 22 effects the linear translational movement of the drive head and drive shaft relative to the main body 18. Rotation of drive head and drive shaft against rigid spring engagement shaft 28 forces internally housed spring 13 into a compressed state.

In device 200, as illustrated in FIGS. 5a and 5b, spring 213 is positioned external to drive shaft 223.

Second end 226 of drive shaft 223 is connected to a second drive head 229. Second drive head 229 comprises a lower spring engaging surface 231 for engagement with spring 213. In this embodiment, lower spring engaging surface 231 is the drive surface.

Spring 213 is connected at its proximal end 216 to lower spring engaging surface 231 of the second drive head 229 and at its distal end 217 to rod engagement element 212. Rotation of first drive head 222 again effects the linear translational movement of the drive head and drive shaft relative to the main body. Rotation of first drive head 222 and drive shaft 223 applies a force against second drive head 229 which imparts a force against spring 213. Force applied by the second drive head 229 on spring 213 causes spring 213 to compress.

Rod engagement element 212 comprises a rod engaging surface 230 which includes a centrally positioned recess 232 which is shaped to conform to a curved outer surface of rod 214.

Both rod reduction device 100 and device 200 further comprise two legs 33a and 33b and 233a and 233b respectively.

Second end 35 of each leg 33a and 33b and second end 235 of legs 233a and 233b are configured to engage with a bone anchor 15 as shown in FIGS. 4a and 4b.

The rod engaging element 12 includes opposed passages 34a and 34b through which respective legs 33a and 33b extend. In a preferred embodiment, the hub body includes two passages to receive two legs therethrough. The passages 34a, 34b are sized such that the rod engaging element 12 is translatable along a length of each leg between the mounting end and the second end.

Similarly in device 200, legs 233a and 233b extend through respective passages 234a and 234b of rod engagement element 212. In this embodiment similar passages are provided in the second drive head 229 to allow passage therethrough of the legs.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An orthopaedic rod reduction device comprising:
a rod engagement element for engaging a rod; and
an actuator, having a drive surface, to apply a drive force to move the rod engagement element;
a spring positioned between the drive surface of the actuator and the rod engagement element to effect movement of the rod engagement element;
wherein substantially all of the drive force applied by the actuator to move the rod engagement element that is transferred to the rod engagement element is transferred through the spring to the rod engagement element.

2. The orthopaedic rod reduction device of claim 1, wherein the actuator comprises a drive head having upper and lower opposed surfaces and further, a drive shaft which extends from a proximal end connected to the lower surface of the drive head member to a distal end which is connected to the rod engagement element.

3. The orthopaedic rod reduction device of claim 2, wherein the drive shaft includes an internal lumen.

4. The orthopaedic rod reduction device of claim 3, wherein the spring is at least partially housed within the internal lumen of the elongate shaft.

5. The orthopaedic rod reduction device of claim 3, wherein the spring extends from a proximal end to a distal end within the internal lumen of the drive shaft wherein the proximal end of the spring engages the lower surface of the drive head, and wherein the distal end of the drive shaft engages the rod engagement element.

6. The orthopaedic rod reduction device of claim 2, wherein a length of the drive shaft includes a threaded outer surface.

7. The orthopaedic rod reduction device of claim 6, further comprising a support having a proximal head and a bone anchor engaging portion which extends distally from the proximal head,
wherein the proximal head includes a passage defined by at least a partially threaded portion of an internal wall of the proximal head, said passage configured to receive at least a length of the drive shaft.

8. The orthopaedic rod reduction device of claim 7, wherein the drive head is rotatably moveable relative to the proximal head of the support and rotation of the drive head relative to the proximal head of the support effects a linear translational movement of the drive head and drive shaft relative to the proximal head.

9. The orthopaedic rod reduction device of claim 2, wherein the spring comprises a helically wound spring member which engages at its proximal end to the drive head and at its distal end to the rod engagement element and which is moveable between a first natural state and a second energy absorbing state, wherein rotation of the drive head and the subsequent linear movement of the drive head causes compression of the spring between the drive head and the rod engagement element to cause the spring to move to its second energy absorbing state.

10. The orthopaedic rod reduction device of claim 9, wherein the second energy absorbing state of the spring is achieved by a pre-determined number of rotations of the drive head, said pre-determined number of rotations effecting a pre-determined translational movement of the drive head, and wherein further rotations of the drive head beyond the pre-determined number of rotations effects a distal linear movement of the rod engagement element.

11. An orthopaedic bone rod reduction assembly comprising:
a support comprising a proximal head having a threaded passage therethrough and a bone anchor engaging portion extending from the proximal head;
a bone rod engagement element for engaging with the bone rod, the bone rod engagement element comprising a base member and a spring engagement element;
an actuator, to apply a drive force to move the bone rod engagement element, comprising a drive head and an elongate drive shaft extending therefrom;
a spring extending from a first end which engages the drive head to a second end which engages the spring engagement element of the rod engagement element, wherein the spring is moveable from a natural state to a compressed state by rotation of the drive head relative to the support to effect movement of the bone rod engagement element;
wherein the spring is moved to its compressed state by a pre-determined number of rotations of the drive head after which, further rotation of the drive head causes a linear movement of the bone rod engagement element;
wherein substantially all of the drive force applied by the actuator to move the bone rod engagement element that is transferred to the bone rod engagement element is transferred through the spring to the bone rod engagement element.

12. An orthopaedic rod reduction device comprising:
a rod engagement element for engaging a rod; and
an actuator, to apply a drive force to move the rod engagement element, having a first drive head and a second drive head, a drive shaft extending between said first and second drive heads;
a spring positioned between the second drive head of the actuator and the rod engagement element to effect movement of the rod engagement element;
wherein substantially all of the drive force applied by the actuator to move the rod engagement element that is transferred to the rod engagement element is transferred through the spring to the rod engagement element.

13. The orthopaedic rod reduction device of claim 12, wherein the first drive head has an upper and a lower opposed surface and the drive shaft extends from a proximal end connected to the lower surface of the drive head to a distal end which is connected to the second drive head.

14. The orthopaedic rod reduction device of claim 13, wherein the second drive head comprises a lower spring engaging surface.

15. The orthopaedic rod reduction device of claim 14, wherein the spring extends from a proximal end which engages the lower spring engaging surface of the second drive head to a distal end which engages the rod engagement element.

16. The orthopaedic rod reduction device of claim 15, wherein the spring comprises a helically wound spring member and is moveable between a first natural state and a second energy absorbing state, wherein rotation of the drive head causes linear movement of the second drive head to compress the spring between the second drive head and the rod engagement element and thus cause the spring to move to its second energy absorbing state.

17. The orthopaedic rod reduction device of claim 16, wherein the second energy absorbing state of the spring is achieved by a pre-determined number of rotations of the first drive head, and wherein further rotations of the drive head beyond the pre-determined number of rotations effects distal linear movement of the rod engagement element.

18. The orthopaedic rod reduction device of claim 12, wherein a length of the drive shaft includes a threaded outer surface.

19. The orthopaedic rod reduction device of claim 12, further comprising a support having a proximal head to receive at least part of the actuator and a bone anchor engaging portion, wherein the proximal head includes a passage defined by at least a partially threaded portion of an internal wall of the proximal head, said passage configured to receive at least a length of the drive shaft.

20. The orthopaedic rod reduction device of claim 19, wherein the bone anchor engaging portion of the support engages the second drive head and the rod engagement element.

\* \* \* \* \*